United States Patent
Petterson et al.

(10) Patent No.: US 7,420,658 B2
(45) Date of Patent: Sep. 2, 2008

(54) METHOD AND DEVICE FOR MEASUREMENTS IN BLOOD

(75) Inventors: Magnus Petterson, Linköping (SE); Anna Dahlström, Linköping (SE); Hans Petterson, Linghem (SE)

(73) Assignee: Optoq AB (SE)

( * ) Notice: Subject to any disclaimer, the term of this patent is extended or adjusted under 35 U.S.C. 154(b) by 347 days.

(21) Appl. No.: 10/528,091

(22) PCT Filed: Dec. 18, 2003

(86) PCT No.: PCT/SE03/02013

§ 371 (c)(1),
(2), (4) Date: Mar. 16, 2005

(87) PCT Pub. No.: WO2004/057313

PCT Pub. Date: Jul. 8, 2004

(65) Prior Publication Data

US 2005/0243303 A1  Nov. 3, 2005

(30) Foreign Application Priority Data

Dec. 20, 2002  (SE) ................................... 02038685
Dec. 20, 2002  (SE) ................................... 02038693

(51) Int. Cl.
*G01N 33/48* (2006.01)

(52) U.S. Cl. .......................................... 356/39; 356/40

(58) Field of Classification Search ............. 356/39–40, 356/432, 440, 246; 600/320
See application file for complete search history.

(56) References Cited

U.S. PATENT DOCUMENTS

| 4,745,279 | A | 5/1988 | Karkar et al. ................ 250/343 |
| 5,601,080 | A | 2/1997 | Oppenheimer ............... 128/633 |
| 6,064,474 | A | 5/2000 | Lee et al. ...................... 356/39 |
| 6,315,955 | B1 * | 11/2001 | Klein ........................... 422/73 |
| 6,365,106 | B1 * | 4/2002 | Nagai ........................... 422/73 |
| 6,388,752 | B1 | 5/2002 | Ziegler et al. ............... 356/436 |
| 6,493,567 | B1 | 12/2002 | Krivitski et al. ............. 600/322 |
| 6,694,157 | B1 * | 2/2004 | Stone et al. ................. 600/310 |

FOREIGN PATENT DOCUMENTS

EP          0575712       12/1993
WO     WO 00/33053       6/2000

* cited by examiner

*Primary Examiner*—Gregory J. Toatley, Jr.
*Assistant Examiner*—Tri T Ton
(74) *Attorney, Agent, or Firm*—Hayes Soloway P.C.

(57) ABSTRACT

We present an optical probe arrangement that surrounds blood in a receptacle. It comprises LED's and light detector arranged to overcome the variations when the receptacle is translucent medical tubing and the like. Also, a signal processing algorithm is used to average signals from a plurality of light detectors, to further enhance results when measuring hematocrit. The invention makes it possible to add the feature of hematocrit measurement into dialysis system without major alterations to the dialysis machine or transport tubing.

21 Claims, 3 Drawing Sheets

METHOD AND DEVICE FOR MEASUREMENTS IN BLOOD

BACKGROUND OF THE INVENTION

Hematocrit is the concentration of red blood cells (RBC) in blood. The measurement of hematocrit values is of great importance in the assessment of the condition of a patient. The established method of measuring hematocrit is by drawing blood from the subject (patient). Various methods to optically measure hematocrit by optical or ultrasonic means have been attempted, e.g., during a dialysis treatment of a patient. In these situations, not only the level of hematocrit is of high importance but also the relative variation of this parameter. In order to provide an optimized but still safe dialysis treatment the change of the hematocrit or relative blood volume has to be monitored during the treatment. The attempts to monitor this have so far not resulted in any product that can measure the hematocrit without a special cuvette integrated in the transport tubing. The methods used so far have therefore increased the cost of every dialysis treatments since the transport tubing must be equipped with this single-use cuvette. The invention presented here does not require any special cuvette, instead it provides the possibility to measure the hematocrit, or monitor the change of relative blood volume directly on any standard dialysis transport tubing on the market without increasing the cost of each treatment.

1. Technical Field

The invention relates to measuring various blood constituents with optical means. Blood is irradiated with—preferably—near infrared or infrared light. Light scattering and attenuation of the light is measured and novel compensations for optical variations in the receptacle walls, flow etc. is used to calculate blood constituents such as hematocrit. The invention makes it possible to add the feature of hematocrit measurement without major alterations into any dialysis system. The addition of this feature makes blood volume measurements at hand.

2. Prior Art

Hematocrit has been measured with various methods since the beginnings of medical diagnosis. Continuous measurement is particularly useful during dialysis treatment. During the process of dialysis, liquids are extracted from the blood stream. As a result, hematocrit increases during the process. For the assurance of good quality in the dialysis treatment, the hematocrit value should be monitored, as this provides the care provider with essential information regarding the rate of extraction of fluids from the patient's bloodstream.

Various techniques have been presented in the field of optical measurements of hematocrit in blood. Several make use of the scattering effect RBC has on light passing trough blood in a vessel, cuvette or the like. Oppenheimer presents in U.S. Pat. No. 5,601,080 a method to measure the degree of scatter to derive blood constituents.

Other patents are U.S. Pat. No. 4,745,279 to Karkar, describing scattering effect of blood in a cuvette. U.S. Pat. No. 6,493,567 to Krivitski et al. describes a measuring instrument using one light emitting diode and one sensor. U.S. Pat. No. 6,064,474 to Wylie et al is another description of a hematocrit measuring method using the scattering effect RBC has on light. However the known methods and devices do not provide a satisfactory precision.

THE INVENTION

The above objects are in accordance with the invention achieved by emitting light into the blood and then two detectors placed opposite each other are used to execute the measuring.

In accordance with the present invention, a new method and a novel apparatus are presented to measure blood properties with a procedure comprising a new optical probe arrangement that overcomes the problem of the prior art, as for instance optical variations, such as optical density, refractions, etc. The invention may even take the shape of a clamp that with great ease can be applied on a transparent tubing such as transport tubing in dialysis. The new problem makes hematocrit values available with unsurpassed precision in the art, in spite of the fact that it measures through transparent tubing that vary in thickness and shape.

In the practical embodiment of the invention the blood is measured as it flows through a transparent tubing. A beam of light, for instance from a laser is directed perpendicular into the tube and two sensors opposed to each other and perpendicular to the light beam pick up light and the sensor signals are used for the evaluation. The light source and the sensors may lie in the same plane but the plane of the sensors may also be slightly offset in relation to the light beam, for instance along the tubing. One can also consider using several pairs of sensors offset along the tubing and upstream as well as downstream in order to increase precision. Also a third sensor may be added to each pair, this third sensor being placed close to the light source.

In this solution the sensor offset in relation to the light source may advantageously be so large that the sensing sectors of the two sensors do not intersect the light beam. With increasing offset the sensitivity to relative changes is increased, whereas a smaller offset will provide a more accurate absolute measurement of the hematocrit value. It is thus possible to use one set of sensors to establish an absolute value and then use a set of more offset placed sensors for the monitoring and controlling of the level during dialysis.

Further preferable developments are apparent from the claims and the following description of a preferred embodiment of the invention.

DESCRIPTION

We have achieved very good results by using the following arrangement of light-emitting diodes (LED's) and photo detectors, when assessing hematocrit values. These values correlate very well with laboratory reference values.

Figure 1:
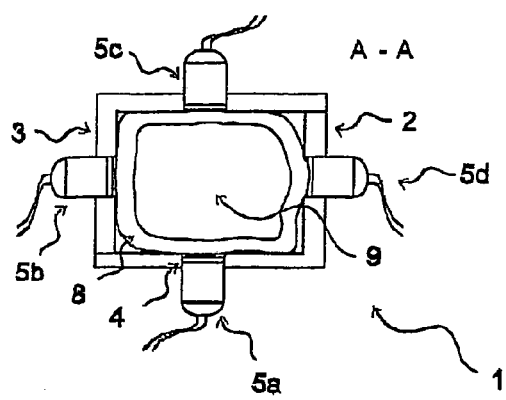
FIG. 1 is a cross section of an optical probe arrangement 1, accommodating light emitting diodes 5 in holes 4 in a framework comprising two halves 2 and 3 suited to fit a receptacle 8 such as tubing for blood 9.
Figure 2:
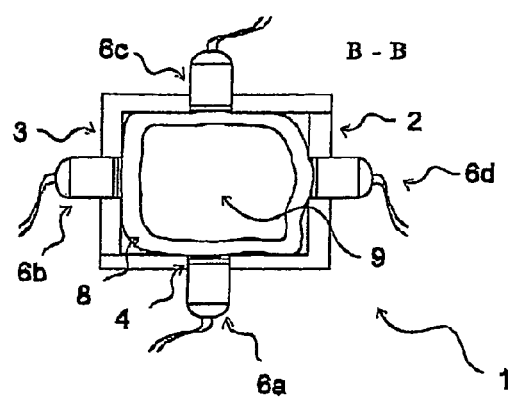
FIG. 2 is a cross section of an optical probe arrangement 1, accommodating light detectors 6 in holes 4 in a framework comprising two halves 2 and 3 suited to fit a receptacle 8 such as tubing for blood 9.
Figure 3:
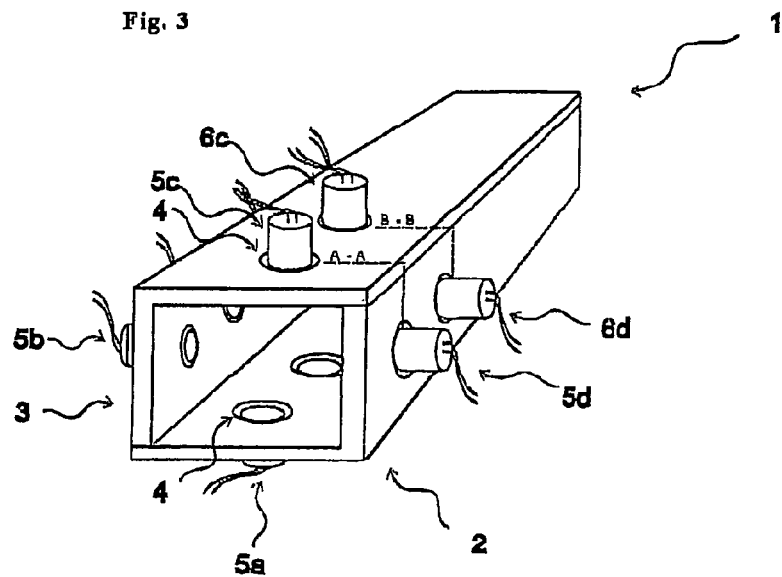
FIG. 3 depicts the arrangement of the array of light detectors 5 and light emitting diodes 6 on the optical probe arrangement 1. This is a suggestion where the arrays according to FIG. 1 and FIG. 2 are located with indication "A-A" for the light emitting diodes, and "B-B" for the light detectors.
Figure 4:
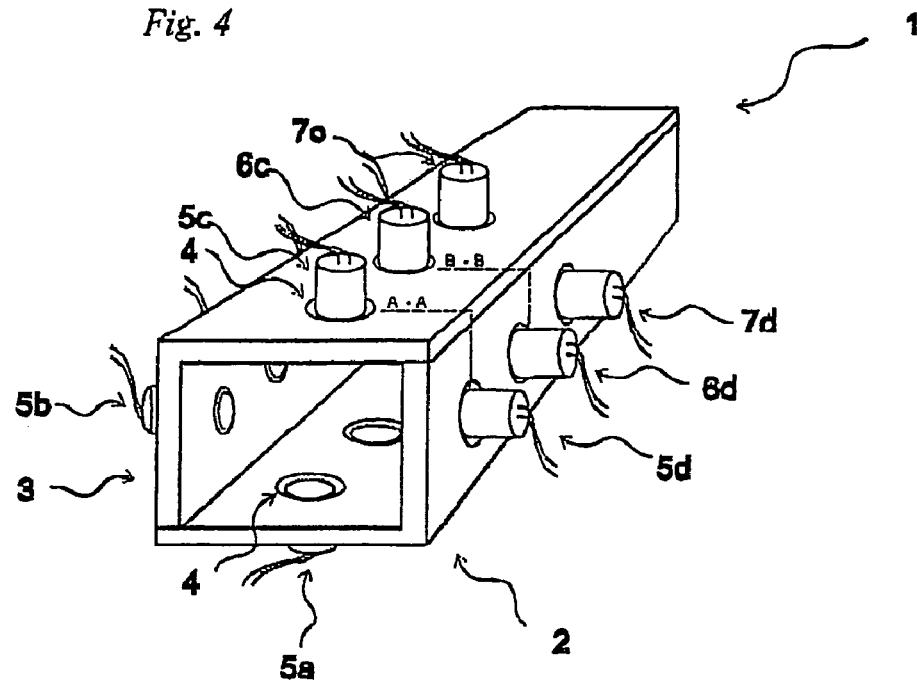
FIG. 4 depicts the arrangement of a second array of light detectors 7.

Four LED's are arranged in a preferably—but not limited to—perpendicular fashion to each other around a receptacle, such as tubing, for the blood as apparent in FIG. 1. The light detectors are arranged in a fashion where they similarly are preferably perpendicular to each other according to FIG. 2, but at a distance longitudinally away from the encirclement by the LED's, as exhibited in FIG. 3. In a further embodiment, a second encirclement of light detectors is fitted. The arrangement is apparent in FIG. 4.

The LED and photo detector arrangement should for best understanding be viewed as groups of LED's and photo detectors: For instance, LED 5 *a*, and photo detector 6 *b* is one group. Another group can be LED 5 *b*, and photo detector 6 *a* and 6 *c*. Note that no LED's and photo detectors are aligned to achieve direct transmitted light. The invention does not make use of directly transmitted light, as often is the case in prior art.

A sample of light detected from a group of one or several photo detectors can be taken at any one short instance in time. Another sample can be taken from the same or another group as a second sample. Preferably, a first sample is taken from a first group comprising LED 5 *a*, and light detectors 6 *b* and 6 *d*, a second sample is taken from a second group comprising LED 5 *b*, and light detectors 6 *a* and 6 *c*, a third sample is taken from a third group comprising LED 5 *c*, and light detectors 6 *b* and 6 *d*, and finally a forth sample is taken from a fourth group comprising LED 5 *d*; and light detectors 6 *a* and 6 *c*. A first result is derived from theses four sequentially acquired samples being signal processed. The process can include variations of amplification factors for the signals from the detectors, and also correlation factors between these signals, to further enhance the detection of the blood constituent to be measured. The results make a first result for blood constituents, such as hematocrit. In this process, the error occurring from variations in the cross section of the flow pattern in the vessel is reduced. Furthermore averaging may reduce the effect the vessel wall has on the measurement. This is highly beneficial if the vessel is the extracorporal circuit of a dialysis system. One of the major advancements in the disclosed invention resides in the new possibility to measure hematocrit trough the walls of dialysis extracorporal circuit, namely the so-called transport tubing of the circuit. It is highly advantageous that no special cuvettes or dedicated arrangements to the disposable bloodlines are necessary. Our process even makes it unnecessary to fit dedicated tubing to the extracorporeal circuit. This feature is considerably cost saving for the health care provider. Fitting the hereby disclosed probe on the transport tubing also has the advantage that the probe is not interfering with the ordinary functions of the dialysis system. Also, it furnishes the highly beneficial possibility to upgrade any already existing dialysis system with measurement of hematocrit, even if it is not prepared for such purpose. Subsequently blood volume changes can be calculated and displayed.

In one embodiment of the invention, two arrays of detectors are employed. Downstream (or upstream) a blood flow in a vessel such as tubing, a second array of detectors is fitted. This is apparent in FIG. 4. The mathematical signal processing can further enhance the results by including this "second order" of detectors in the process.

Figure 5:
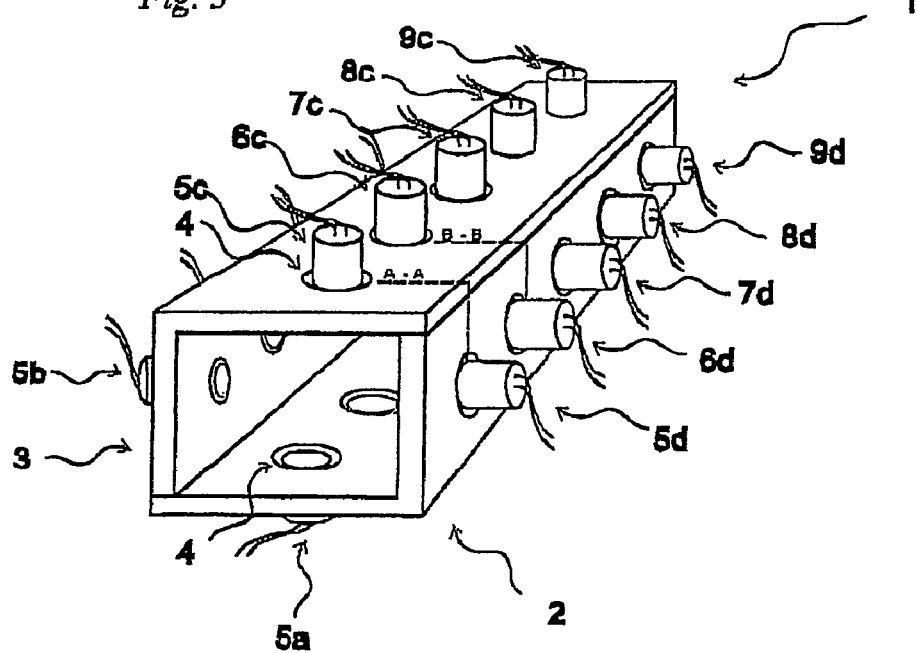
FIG. 5 depicts the optical probe arrangement 1 with the further embodiment of light emitting diodes 9, and photo detectors 8.
Figure 6:
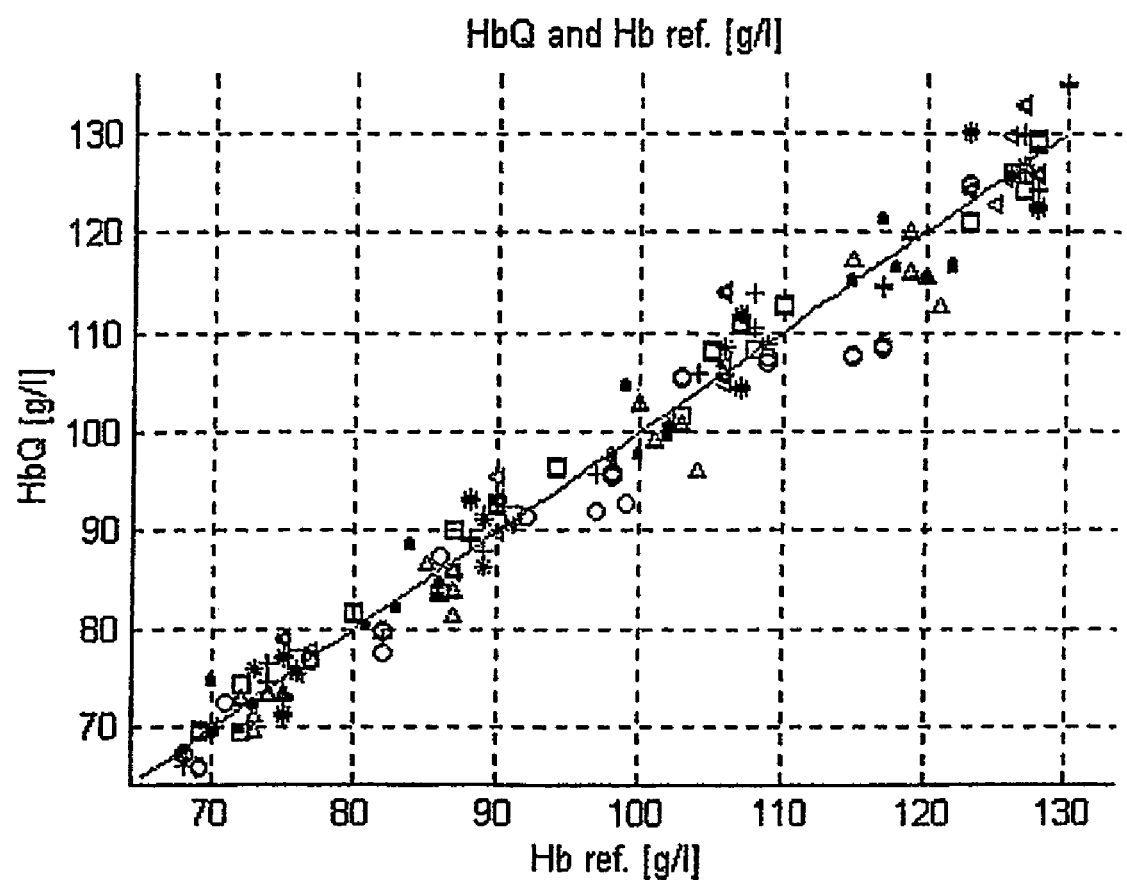
FIG. 6 depicts the resulting hematocrit values with reference to measurements performed at an accredited clinical laboratory.

In another embodiment of the invention, a second arrangement of LED's and photo detectors, including a second array of detectors is fitted. This is exhibited in FIG. 5. In this embodiment, the LED's emits a different wavelength. This allows limited spectral analysis for further calculation of blood constituents, such as saturation of hemoglobin as known in the art. The results derived from this second array, can beneficially be incorporated in a signaling process with the values derived from the aforementioned first array. Such process makes it possible not only to output all parameters from blood constituents, but also let the saturation value influence the input of signals from the first array to the signaling process. This is beneficial, as blood saturation may influence the first results of blood constituents from the first process from the first array.

In the drawings and the above description a transparent blood transporting tubing is shown clamped between two essentially V-shaped profiles in the walls of which the led and sensors are arranged. In an alternative embodiment V-shaped groves in blocks may be used to clamp and shape the tubing so that its walls become essentially flat at LEDs and sensors.

In a further embodiment the sensors may be arranged in small holes with even smaller openings serving as collimators towards the tubing.

It is not today clear why the invented measuring method and device are so superior in relation to the prior art, one theory could be the offset between sensors and light source. Only one light that has been dispersed from the volume of the blood in the path of the light and into the sense sector of the sensor and from this into the sensor will be registered. In other words only light that has been dispersed at least twice will reach the sensor. By arranging source and sensor perpendicularly blood cells in a major part of the tube cross section will have the opportunity to contribute so that the signals from the sensors become a function of the hematocrite value.

The invention claimed is:

1. An optical sensor device for measuring blood constituents in an elongated vessel of tubing, said optical sensor device comprising at least two sets of light emitters and light detectors, each set comprising one light emitter and at least one detector, wherein a first set of light emitters are arranged as an array encircling the elongated vessel or tubing a longitudinal location along the vessel or tubing, and at least a second set light detectors are arranged as arrays encircling the elongated vessel or tubing at a longitudinally different location along the vessel or tubing, and said light emitters and said light detectors are aimed so that the detectors do not directly intercept light from the emitters.

2. The optical sensor device according to claim 1, comprising four sets of light emitters and two or three light detectors in each set, wherein a light detector in each set represents a detector incorporated in an adjacent set.

3. The optical sensor device according to claim 1, wherein a second array of light detectors are longitudinally located at a third location around said vessel's or tubing's circumference, and the light detectors are arranged to encircle the vessel or tubing at that circumferential location.

4. A method for processing signals from light detectors as claimed in claim 1, including an amplifier for amplifying signals from the light detectors, which comprises employing a signal processing algorithm on the signals from said light detectors, to detect blood constituents.

5. The method for processing signals from light detectors as claimed in claim 4, which comprises employing a signal processing algorithm on the signals from said light detectors, to detect hematocrit.

6. The method according to claim 5, which comprises employing a multi variable analysis of signals from all light detectors engaged in the signaling process.

7. The method according to claim 4, wherein signals are processed in a time domain.

8. The optical sensor device as claimed in claim 1, wherein a third array of light detectors are longitudinally located at a fourth location around a receptacle's circumference, and the light detectors are arranged to encircle the receptacle at that circumferential location, and an second array of light emitters are longitudinally located at a fifth location around said receptacle's circumference, and the light detectors are arranged to encircle the receptacle at that circumferential location.

9. A method for processing signals from light detectors as claimed in claim 8, including an amplifier for amplifying signals from the light detectors, and which comprises employing a signal processing algorithm on the signals from said light detectors, to detect blood constituents.

10. The method according to claim 9, wherein signals are processed in a time domain.

11. The method of claim 10, wherein the signals are processed sequentially.

12. A method for processing signals from optical sensor devices as claimed in claim 1, including an amplifier for amplifying signals from the light detectors, which comprises employing a signal processing algorithm on the signals from said light detectors, to detect oxygen saturation in blood.

13. The method according to claim 12, wherein signals are processed in a time domain.

14. The method of claim 13, wherein the signals are processed sequentially.

15. The optical sensor device as claimed in claim 1, further comprising a system to calculate hematocrit values from blood, and presenting the data to a display, and/or transferring data to another application.

16. The optical sensor device as claimed in claim 15, characterized in that the measuring takes place in a vessel or tubing that is clamped in a holder with V-shaped recesses so that the vessel or tube is flattened to a square cross section, and that light sources and sensors are arranged at flattened surfaces of the vessel or tubing.

17. The optical sensor device as claimed in claim 1, further comprising a system to calculate hematocrit values and oxygen saturation values from blood, and presenting the data to a display, and/or transferring data to another application.

18. The optical sensor device as claimed in claim 17, characterized in that the measuring takes place in a vessel or tubing that is clamped in a holder with V-shaped recesses so that the vessel or tubing is flattened to a square cross section, and that light sources and sensors are arranged at flattened surfaces of the vessel or tubing.

19. The optical sensor device as claimed in claim 1, characterized in that the measuring takes place in a vessel or tubing that is clamped in a holder with V-shaped recesses so that the vessel or tubing is flattened to a square cross section, and that light emitters and sensors are arranged at flattened surfaces of the vessel or tubing.

20. The optional sensor device as claimed in claim 1, wherein the light emitters emit at different wavelengths.

21. A optical sensor device as claimed in claim 1, further comprising a holder with V-shaped recesses for flattening the vessel or tubing to a square cross section, and the light emitters and sensors are arranged at flattened surfaces of the vessel or tubing.

* * * * *

UNITED STATES PATENT AND TRADEMARK OFFICE
CERTIFICATE OF CORRECTION

PATENT NO. : 7,420,658 B2
APPLICATION NO. : 10/528091
DATED : September 2, 2008
INVENTOR(S) : Pettersson et al.

It is certified that error appears in the above-identified patent and that said Letters Patent is hereby corrected as shown below:

Title Page, Item (75)
The Inventors "Magnus Petterson" and "Hans Petterson" should be --Magnus Pettersson and Hans Pettersson--.
Claim 4, Col. 4, line 59, "A method for processing" should be --The method for processing--.

Signed and Sealed this

Thirteenth Day of January, 2009

JON W. DUDAS
*Director of the United States Patent and Trademark Office*